United States Patent [19]

Nankai et al.

[11] Patent Number: 5,120,420
[45] Date of Patent: Jun. 9, 1992

[54] BIOSENSOR AND A PROCESS FOR PREPARATION THEREOF

[75] Inventors: Shiro Nankai, Hirakata; Mariko Kawaguri; Mayumi Ohtani, both of Moriguchi; Takashi Iijima, Hirakata, all of Japan

[73] Assignee: Matsushita Electric Industrial Co., Ltd., Osaka, Japan

[21] Appl. No.: 445,632

[22] PCT Filed: Mar. 31, 1989

[86] PCT No.: PCT/JP89/00337

§ 371 Date: Jan. 31, 1990

§ 102(e) Date: Jan. 31, 1990

[87] PCT Pub. No.: WO89/09397

PCT Pub. Date: Oct. 5, 1989

[30] Foreign Application Priority Data

Mar. 31, 1988 [JP] Japan ................. 63-080829
Mar. 31, 1988 [JP] Japan ................. 63-080842
May 18, 1988 [JP] Japan ................. 63-121002

[51] Int. Cl.⁵ ........................... G01N 27/26
[52] U.S. Cl. ...................... 204/403; 204/153.12; 204/153.17; 204/415; 435/817; 435/180; 436/531; 436/806
[58] Field of Search .......... 204/153.12, 153.17, 204/403, 415; 435/817, 180; 436/531, 806

[56] References Cited

U.S. PATENT DOCUMENTS 3,979,274  9/1976  Newman ................. 435/180
4,418,148  11/1983  Oberhardt ............... 435/180
4,545,382  10/1985  Higgins et al. ......... 435/180
4,897,173  1/1990  Nankai et al. ......... 204/412
4,900,405  2/1990  Otagawa et al. ....... 204/153.16

FOREIGN PATENT DOCUMENTS 62-137559  6/1987  Japan ................. 27/26
63-3248  1/1988  Japan ................. 27/26
63-58149  3/1988  Japan ................. 27/26

Primary Examiner—John Niebling
Assistant Examiner—Bruce F. Bell
Attorney, Agent, or Firm—Stevens, Davis, Miller & Mosher

[57] ABSTRACT

A biosensor of the invention comprises an insulating base board (1) having formed thereon, in sequence, leads (2, 3, 3'), an electrode system mainly made of carbon (4, 5, 5'), an insulating layer (6) and a reaction layer (14) composed of an enzyme and an electron acceptor, and being provided thereon with a space (8) defined by a spacer (7) and a cover (9). When a biological sample solution is brought into contact with the inlet (10) of the biosensor having the above-described structure, the sample solution is introduced into its inside, while the air within the space (8) is rapidly discharged through the outlet (11) and, at the same time, the space (8) is filled with the sample solution up to the neighborhood of the outlet. Thus, measurement can be conducted inexpensively at a high speed with a high accuracy through simple procedures without residual bubbles.

18 Claims, 13 Drawing Sheets

BIOSENSOR AND A PROCESS FOR PREPARATION THEREOF

FIELD OF THE INVENTION

The present invention relates to biosensors which can quantitatively determine a specific component in various sample solutions from the living body in a rapid and easy way with high accuracy and a process for preparation thereof.

BACKGROUND OF THE INVENTION

In recent years, various biosensors utilizing a specific catalytic action possessed by enzyme have been developed and in particular, it has been attempted to apply biosensors to the clinical field. In the present days when inspection items and sample numbers are increasing, biosensors which can provide rapid assay with good accuracy have been desired.

Taking a glucose sensor as an example, diabetes has markedly increased nowadays and for measurement and control of blood sugar level in blood, it takes a very long time, since blood is centrifuged and plasma is provided for the measurement as is conventionally done. Thus, a sensor which can make measurement with whole blood is required. As a handy type, there is a stick-like support having provided thereon a carrier containing an enzyme capable of reacting only with glucose and a dye which causes a change upon enzyme reaction or by the product of the enzyme reaction, like a test sheet used for inspection of urine. The stick takes the system that blood is dropped onto the carrier and after a definite period of time, a change of the dye is visually or optically determined. However, interference is serious because of colored matters in blood, resulting in poor accuracy.

Now, a multilayer type analysis carrier as shown in FIG. 1 is proposed (Japanese Utility Model Application Laid-Open No. 54-178495). The carrier has the construction comprising a transparent support 51 having provided thereon, in order, a reagent layer 52, a spreading layer 53, a waterproofing layer 54 and a filtering layer 55. The measurement takes the following system: when a blood sample is dropped from the upside, solid components in blood such as red blood cells, platelets, etc. are removed by the filtering layer 55, the blood uniformly permeates into the spreading layer 53 through a hole 56 in the waterproofing layer and a reaction proceeds in the reagent layer 52. After completion of the reaction, a light is irradiated from the arrow direction through the transparent support 51, whereby a substrate concentration is determined by colorimetry. The system takes a complicated construction as compared to the conventional handy stick-like carrier but its accuracy has improved because blood cells are removed, etc. However, it takes a long time for the permeation of blood and the reaction so that the waterproofing layer 54 that prevents drying of the sample is required. In addition, incubation at a high temperature is required for accelerating the reaction. Thus, the system involves problems that apparatuses and carriers become complicated.

On the other hand, as the system for quantitative assay of a specific component in a sample such as blood, etc. from the living body with high accuracy without performing operations such as dilution, agitation, etc. of the sample solution, a biosensor as shown in FIG. 2 has been proposed (for example, Japanese Patent Application Laid-Open No. 59-166852). The biosensor comprises an insulating base plate 63 having embedded therein an electrode for measurement 64 and a counter electrode 65 made of platinum, etc., having leads 61 and 62, respectively, and the exposed areas of these electrodes are covered with a porous material 66 having carried thereon an oxidoreductase and an electron acceptor. When a sample solution is dropped onto the porous material, the oxidoreductase and the electron acceptor are dissolved in the sample solution, whereby an enzyme reaction proceeds with a substrate in the sample solution and the electron acceptor is reduced. After completion of the reaction, the reduced electron receptor is electrochemically oxidized and a substrate concentration in the sample is determined from a current level for the oxidation obtained in this case. In such a construction, however, the electrodes require operations such as washing, etc., while the porous material can be exchanged for every assay thereby to readily provide for measurement. On the other hand, if it is possible to dispose the apparatus including the electrode system for every measurement, operations for the measurement become extremely simple but from aspects of electrode materials such as platinum, etc., construction and the like, the apparatus is very expensive unavoidably. For the construction of platinum electrodes, the sputtering method or the deposition method can also be used but production costs increase.

As a disposal system including the electrode system, a biosensor described in Japanese Patent Application Laid-Open No. 61-294351 has been proposed. As shown in FIG. 3, in this biosensor, the electrode systems 72 (72'), 73 (73') and 74 (74') composed of carbon, etc. are formed on an insulating base plate 71 by means of screen printing, etc.; after providing an insulating layer 75 thereon, the electrode systems are covered with a porous material 77 having carried thereon an oxidoreductase and an electron acceptor and the whole is integrated with a holding frame 76 and a cover 78. When a sample solution is dropped onto the porous material, the oxidoreductase and the electron acceptor are dissolved in the sample solution, whereby an enzyme reaction proceeds with a substrate in the sample solution and the electron acceptor is reduced. After completion of the reaction, the reduced electron acceptor is electrochemically oxidized and a substrate concentration in the sample is determined from a current level for the oxidation obtained in this case.

In the foregoing conventional construction, the base surface including the electrode system is not always uniformly wetted so that air bubbles remain between the porous material and the base plate, whereby a response current is affected or its reaction rate is reduced in some occasion. Further when an ambient humidity is low, moisture in a sample solution evaporates off during measurement so that a change in response is observed. Furthermore, when a substance that is readily adsorbed to electrodes or a substance such as ascorbic acid or the like that is easily oxidized is present in a sample solution, response of the sensor is affected by such a substance.

Therefore, as sensors for measuring a specific component in a vital sample solution such as blood or the like in a simple and rapid way with high accuracy, sensors which can provide measurement data merely by adding a trace amount of sample solution thereto without diluting or quantitatively determining the sample solution previously are desired. Furthermore, disposable type sensors which are free of operations such as washing, wiping, etc. are desired.

DISCLOSURE OF THE INVENTION

The biosensor of the present invention comprises an insulating base plate having provided thereon the electrode system comprised of at least an electrode for measurement and a counter electrode and on the electrode system a reaction layer containing an enzyme and an electron acceptor. Further by integrating with a cover, a space including the reaction layer is formed and an introducing port for introducing a sample solution into the space and a discharge port for discharging a gas in the space by inflow of the sample solution. A change of a substance in concentration caused by the reaction between the enzyme and the sample solution is detected by the electrode system thereby to determine a substrate concentration in the sample solution.

Furthermore, the electrode system may also be comprised of a plural set of electrode systems and reaction layers corresponding to the plural set of electrode systems are provided, whereby the independent sensor systems can be constructed. By doing so, two or more substrate concentrations can be concurrently determined. Furthermore, two pairs of electrode systems may also be used, wherein one electrode system is used for measurement and another electrode system is used for blank. By determining a difference in response between the electrode systems, interference by ascorbic acid, etc. can be eliminated.

Further by integrating the base plate, the electrode system and the reaction layer with the cover, a space is formed and the surface of members constructing the space is rendered hydrophilic, whereby a definite quantity of sample solution can be readily introduced into the space described above through a simple operation merely by bringing a trace amount of sample solution into contact with the introducing port of the sensor.

The introduced sample solution dissolves the electron acceptor, enzyme and hydrophilic high molecular substance in the reaction layer, where an enzyme reaction proceeds while converting the sample solution into a viscous liquid. By the enzyme reaction, a reduced electron acceptor is produced in response to the substrate concentration in the sample solution. Then, the reduced electron acceptor is electrochemically oxidized on the electrode for measurement to determine the substrate concentration from a current level for the oxidation.

In the biosensor of the present invention, a hydrophilic high molecular substance is used s that influence of solid components such as red blood cells and the like in a blood sample on the electrodes can be prevented and at the same time, by providing the space, fluidization of the sample solution on the electrodes can be effectively prevented. Thus, an influence by vibration during measurement can be prevented.

On the other hand, the reaction layer in the biosensor of the present invention is comprised of an enzyme layer and an electron acceptor layer provided thereon. Further by providing a hydrophilic high molecular substance layer between these layers, the enzyme and the electron acceptor are separated from each other to provide a biosensor having excellent preservation property.

According to the present invention, a disposable biosensor including the electrode system can be constructed so that a substrate concentration in the sample, for example, a glucose concentration in blood can be determined rapidly in a simple operation with high accuracy, merely by adding an extremely trace amount of sample solution, without diluting or quantitatively determining the sample solution in advance.

BEST MODES FOR PRACTICING THE INVENTION

EXAMPLE 1

In the following explanatory drawings in the examples, the same numbering is used for common elements and their explanation is in part omitted.

Figure 4:
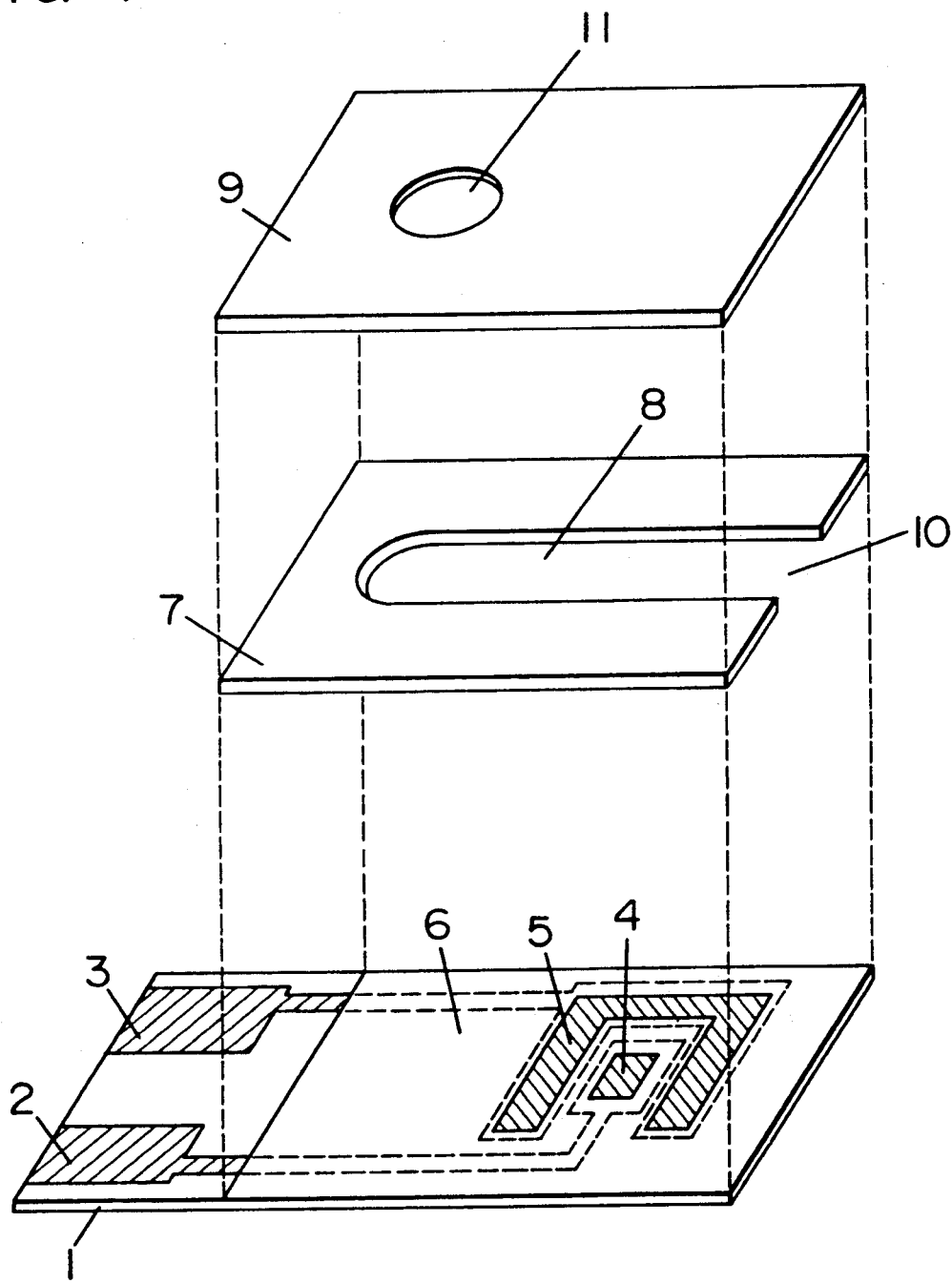
FIG. 4 shows a perspective view of a disassembled biosensor which is one embodiment of the present invention.
Figure 5:
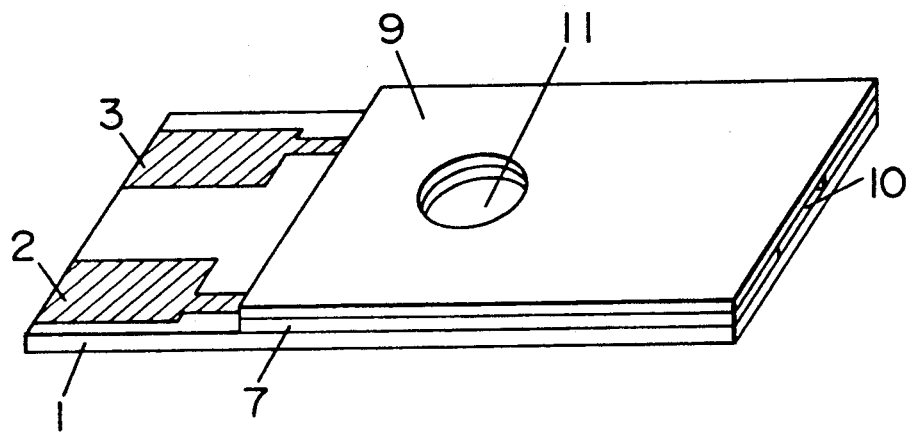
FIG. 5 shows an external view of the biosensor.
Figure 6:
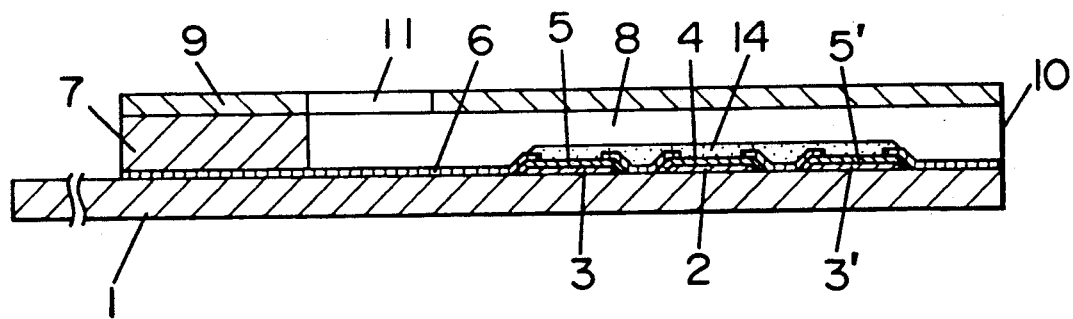
FIG. 6 illustratively shows a cross-sectional view of the biosensor.

As one embodiment of the biosensor, a glucose sensor is explained. FIG. 4 shows a perspective view of a disassembled glucose sensor prepared as one embodiment of the biosensor in accordance with the present invention. FIG. 5 shows an external view of the biosensor. FIG. 6 illustratively shows a cross-sectional view of the biosensor obtained when the biosensor shown in FIG. 5 is cut at the center into the length direction. In FIG. 4, a reaction layer 14 shown in FIG. 6 is not shown.

Hereafter a process for preparing the sensor is described. Silver paste is printed on an insulating base plate 1 composed of polyethylene terephthalate by means of screen printing to form leads 2, 3 (3'). Next, conductive carbon paste containing a resin binder is printed thereon. By drying with heating, the electrode system comprised of an electrode for measurement 4 and a counter electrode 5 (5') is formed. Furthermore, insulating paste is printed so as to partly cover the electrode system to make the exposed area of the electrodes definite and cover unnecessary part of the leads. By a heat treatment, an insulating layer 6 is formed.

Next, the exposed area of the electrode system 4, 5 (5') is polished and then heat-treated at 100° C. for 4 hours in the air. After the electrode portion is thus constructed, 0.5% aqueous solution of carboxymethyl cellulose (hereafter simply referred to as CMC) as the hydrophilic high molecular substance is spread onto the electrodes and dried to form a CMC layer. A solution of glucose oxidase (GOD) as the enzyme in phosphate buffer solution is spread thereon and dried to form a reaction layer 14 comprised of CMC-GOD layer. In this case, CMC and GOD form a thin layer having a thickness of several microns in a partly mixed state.

Next, three members of this base plate 1, a spacer 7 comprised of a resin plate and a cover 9 are adhered to each other in such a positional relationship between the respective members shown by broken lines as shown in FIG. 4 to integrate the sensor as shown in the external view in FIG. 5. Herein, the spacer has a thickness of approximately 300 μm and takes a shape that the central part is cut off into a V-letter shape having a width of 2 mm and a length of 7 mm. The end of the cut portion becomes an introducing port 10 of a sample solution and the central part forms a space 8, when integrated. Furthermore, the cover 9 possess a hole having a diameter of 2 mm and forms a discharge port 11 when integrated.

When the introducing port at the tip of the glucose sensor constructed as described above is brought into contact with a glucose standard solution (200 mg/dl) which is a sample solution, the sample solution is introduced into the inside through the introducing port 10. In this case, the air in the space 8 is rapidly discharged through the discharge port 11 and at the same time, the space is filled up with the sample solution up to near the discharge port. As such, the sample solution rapidly spreads onto the electrode surface to fill up the space so that any remaining air bubbles are not noted.

This is believed to be because the sample solution would flow into one direction by providing the introducing port and the discharge port and due to the hydrophilic high molecular substance layer previously formed on the electrodes, wetting on the electrode surface would be improved so that the gas is smoothly exchanged with the liquid.

Further by previously treating the surfaces of the members constructing the space such as the cover, spacer, etc., with a surface active agent to render them hydrophilic, the sample solution can be introduced more smoothly.

On the other hand, the added sample solution dissolves CMC therein to render the liquid viscous. Glucose in the sample solution reacts with the enzyme by the action of glucose oxidase carried on the electrodes to produce hydrogen peroxide. Therefore, by applying a voltage of 1 V between the electrodes one minute after introduction of the sample solution, the electrode for measurement is polarized into the anode direction. By applying a voltage to the anode direction described above, an oxidizing current for the produced hydrogen peroxide is obtained. This current level corresponds to the concentration of glucose which is a substrate.

Figure 7:
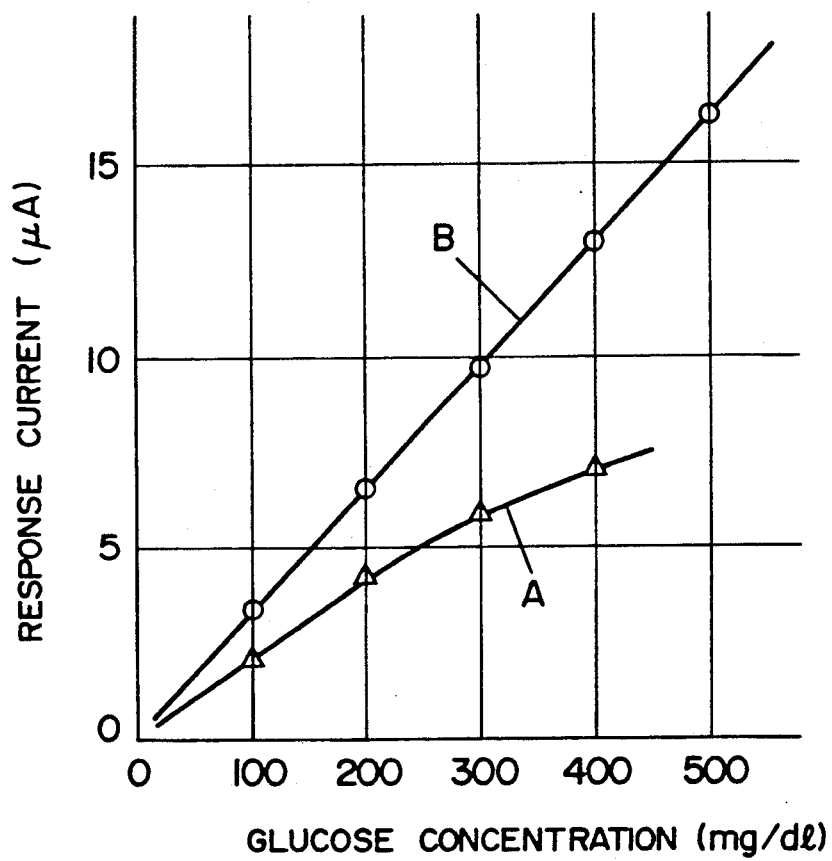
FIG. 7 shows a response characteristic of the biosensor.

As an example of the response characteristic of the sensor constructed as described above, the relationship between a current level 5 seconds after application of voltage and a glucose concentration is shown in FIG. 7, A, indicating that a good response characteristic was obtained.

Further with respect to 30 glucose sensors having the same specification as described above, the same sample solution was tested with the sensors. A coefficient of variation was as good as about 5%.

Figure 1:
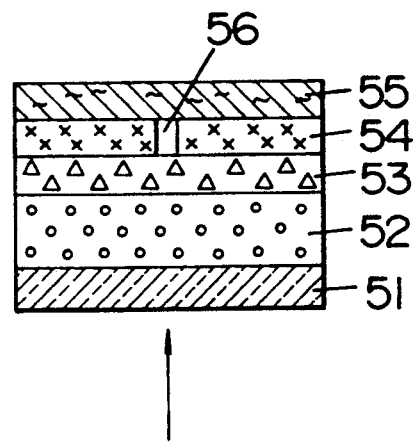
FIG. 1 is an illustrative drawing showing an example of conventional glucose sensors.
Figure 2:
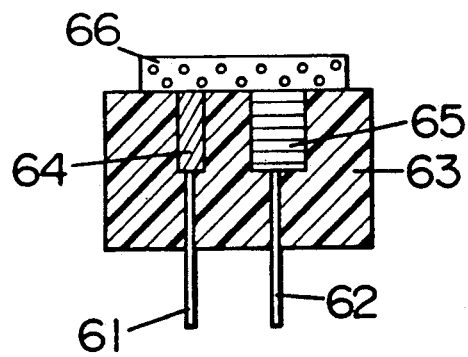
FIGS. 2 and 3 illustratively show glucose sensors using conventional enzyme electrodes.
Figure 3:
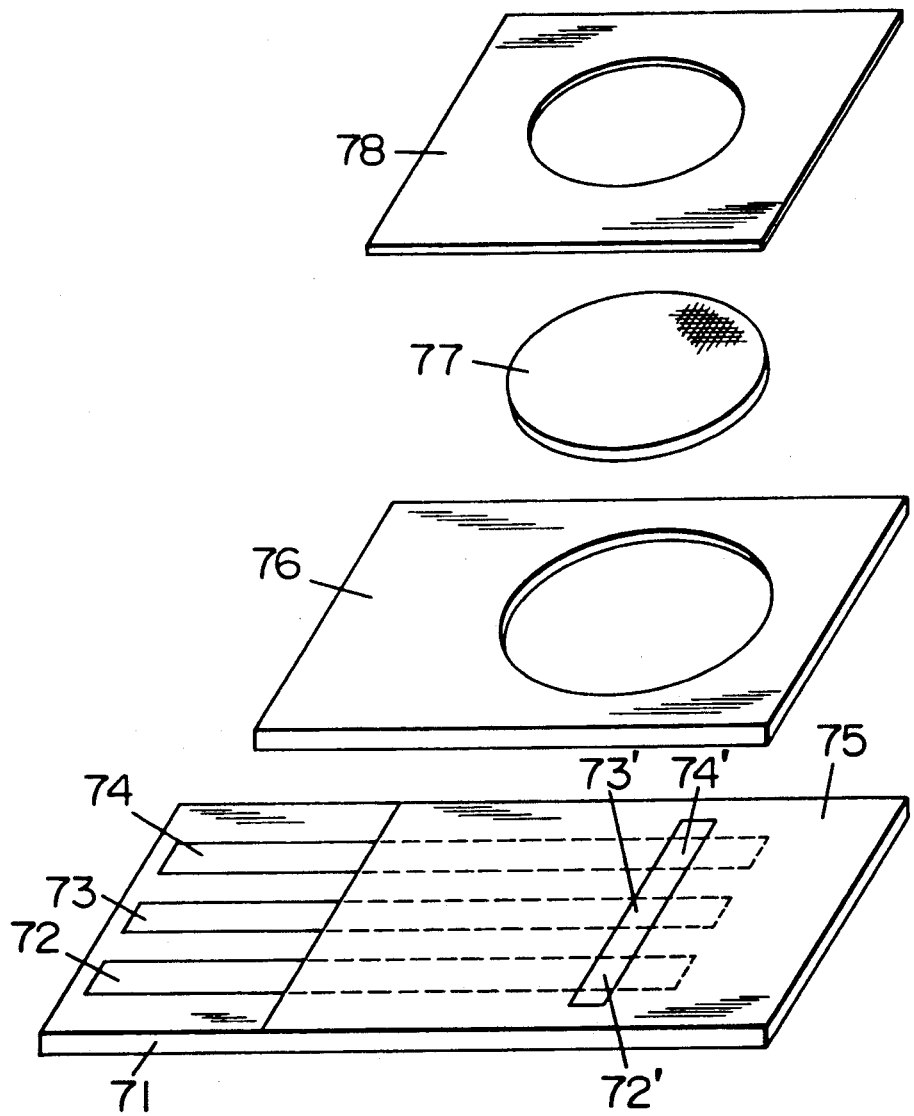

Furthermore, influence by evaporation was examined under humidity conditions of 30% and 80%, using 10 sensors each, and compared with the glucose sensor shown in FIG. 3 which was prepared in a conventional construction by way of trial. In the glucose sensors according to the present invention, the influence was negligible even after allowing to stand for 5 minutes. However, in the sensors having a conventional construction, the evaporation was higher by about 3% under the lower humidity condition 2 minutes after.

As described above, the glucose sensor of the present invention having the construction described above can rapidly absorbs a trace amount of the sample solution into the reaction layer zone and can determine a glucose concentration in a simple and rapid way with high accuracy, without being affected by ambient humidity, etc.

EXAMPLE 2

The procedure was quite the same as in Example 1 until the CMC-GOD layer was formed. Thereafter, a reaction layer composed of a CMC-GOD-electron acceptor layer was further formed thereon by the following method.

Surface active agent, lecithin (phosphatidyl choline), was dissolved in toluene to prepare 1 wt % solution and microcrystals (a mean particle diameter of less than 10 μmm) of potassium ferricyanide as an electron acceptor was dispersed in the solution. Then toluene was evaporated off to form the reaction layer composed of CMC-GOD-electron acceptor layer on the electrode system followed by integrating with a spacer and a cover as in Example 1. Thus, a glucose sensor having the construction shown in FIG. 5 was obtained.

Next, a glucose standard solution was introduced through the tip portion of the sensor as described above. By applying a voltage of 600 mv between the electrodes about one minute after, potassium ferricyanide produced by the enzyme reaction was oxidized on the electrode for measurement. A current level in this case was measured 5 seconds after application of the voltage. As the result, an extremely good linear relationship was obtained between the glucose concentration and the response current level, as shown in FIG. 7, B. Further using 30 sensors, a variation coefficient was examined. The coefficient of variation was 2.6% with respect to the glucose standard solution and 3% with respect to the whole blood sample, which were extremely good. Further with respect to influence of evaporation, a test was carried out in a manner similar to Example 1 and similar effects were obtained, as described above.

In the above example, when the concentration of lecithin was greater than 0.01 wt %, potassium ferricyanide was efficiently dispersed in toluene so that dropping became easy to form a thin potassium ferricyanide-lecithin layer. Where no lecithin is present, defects that the potassium ferricyanide layer was non-uniformly formed or the base plate was peeled off when bent were noted. However, by incorporating lecithin, the potassium ferricyanide layer which was uniform and peeled off only with difficulty could readily be formed. As the concentration of lecithin increased, the potassium ferricyanide layer was peeled off more difficultly but a dissolution rate of potassium ferricyanide also decreased. Therefore, a suitable concentration is believed to be 0.01 to 3 wt %. Polyethylene glycol alkyl phenyl ether (trademark: Triton X) was used instead of lecithin. In order to disperse fine particles of potassium ferricyanide in toluene, more than 0.1% was necessary but a good potassium ferricyanide layer could be formed as in the case of using lecithin. As the surface active agent, there are oleic acid, polyoxyethylene glycerine fatty acid ester, cyclodextrin, etc., in addition to the example described above. Surface active agents are not particularly limited so long as they can disperse the electron acceptor in an organic solvent and do not affect the enzyme activity. As the organic solvent for mixing the electron acceptor therewith, solvents such as toluene, petroleum ether, etc. may be used as long as they have a minimized influence on GOD activity and the printed electrodes.

Figure 15:
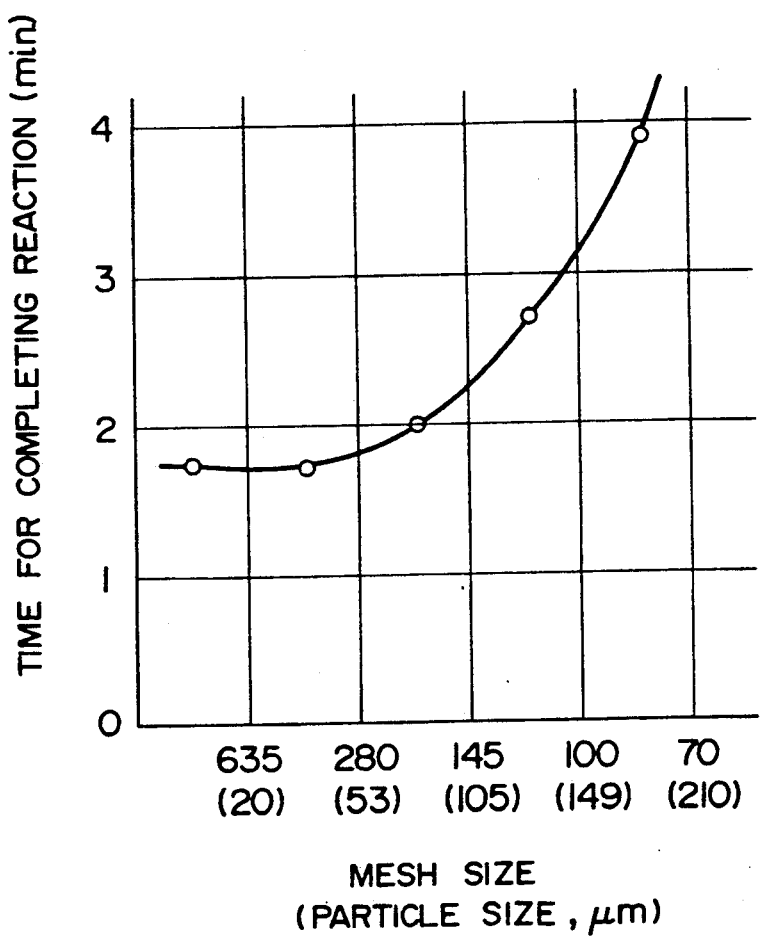
FIG. 15 shows a relationship between the particle diameter of potassium ferricyanide and the time when the reaction is completed.

With respect to the particle diameter of microcrystalline potassium ferricyanide used above, commercially available crystals of potassium ferricyanide were ground into powders and crystals of a definite particle diameter were collected by sieving to form a potassium ferricyanide layer. With respect to the same glucose sensors as described above prepared from crystals of various particle diameters, their responses were compared with each other. FIG. 15 shows a mesh size of sieve on the abscissa and on the ordinate, a time for completing the reaction to 400 mg/dl of glucose. Numerals with parentheses indicate a size ($\mu$m) of the mesh hole. As shown in FIG. 15, crystals having a smaller particle size were dissolved more quickly and the time required for completing the reaction was shorter. In the sensor prepared with potassium ferricyanide (particle size of 100 $\mu$m or less) passed through 145 mesh (Japanese Industrial Standard), the reaction was completed within 2 minutes. In addition, when the potassium ferricyanide layer was prepared, crystals having a smaller particle diameter could form a uniform layer and provided less unevenness in response. Microcrystals of potassium ferricyanide could be formed by grinding into powders but recrystallization of an aqueous potassium ferricyanide solution from ethanol could easily prepare crystals having a particle diameter of not greater than 10 $\mu$m. When the potassium ferricyanide layer was formed from such crystals, the layer became dense and the time for completing the reaction could be shortened.

When potassium ferricyanide finely divided into a particle diameter of less than 100 $\mu$m was mixed with toluene and the mixture was dropped, toluene was rapidly evaporated and the potassium ferricyanide layer could be formed in a microcrystalline state so that a dissolution rate was rapid and rapid measurement was attained. Further by using the organic solvent, the potassium ferricyanide layer could be formed separately on the CMC-GOD layer, whereby preservation property could be improved.

Figure 8:
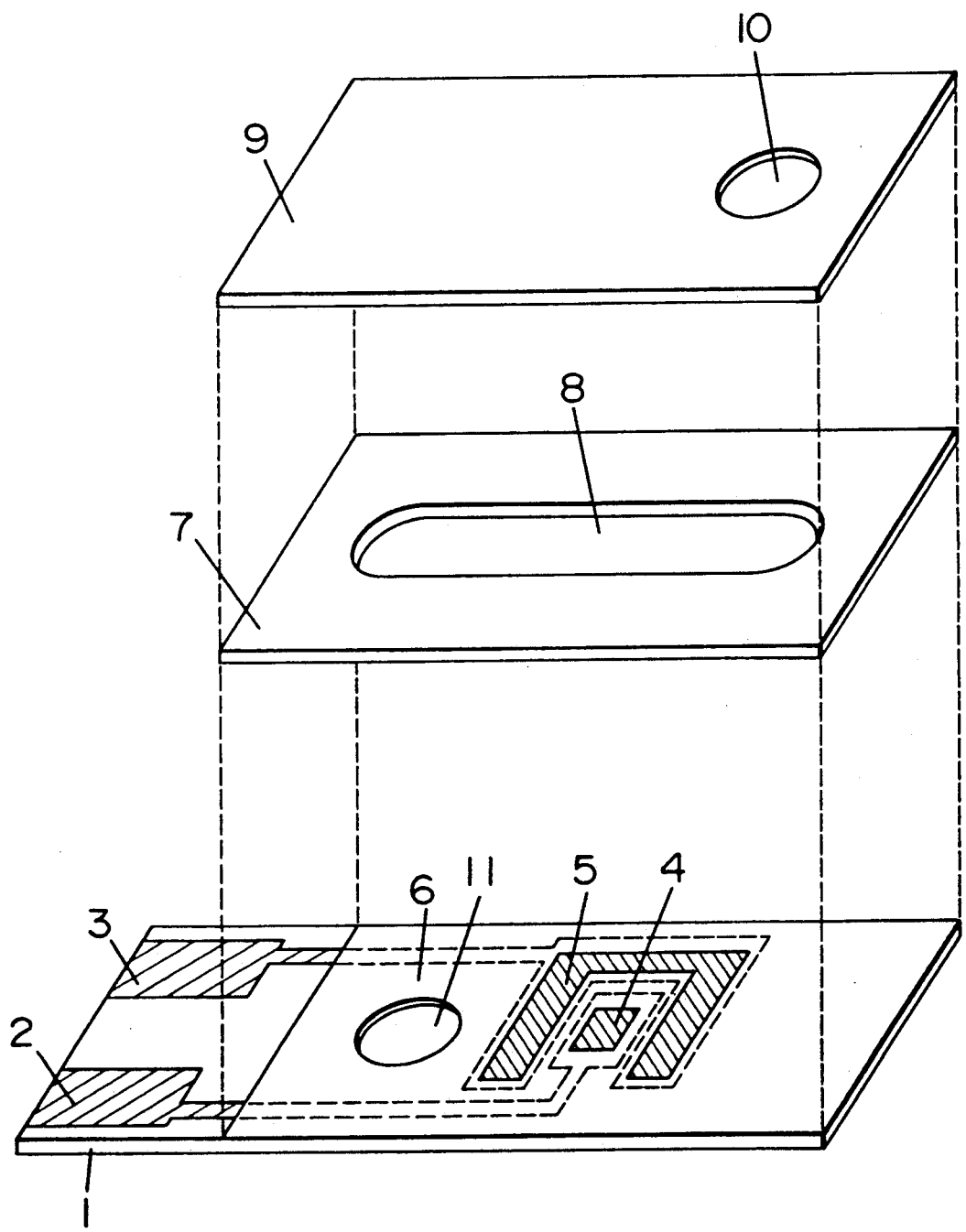
FIG. 8 shows a perspective view of a disassembled biosensor which is another embodiment of the present invention.
Figure 9:
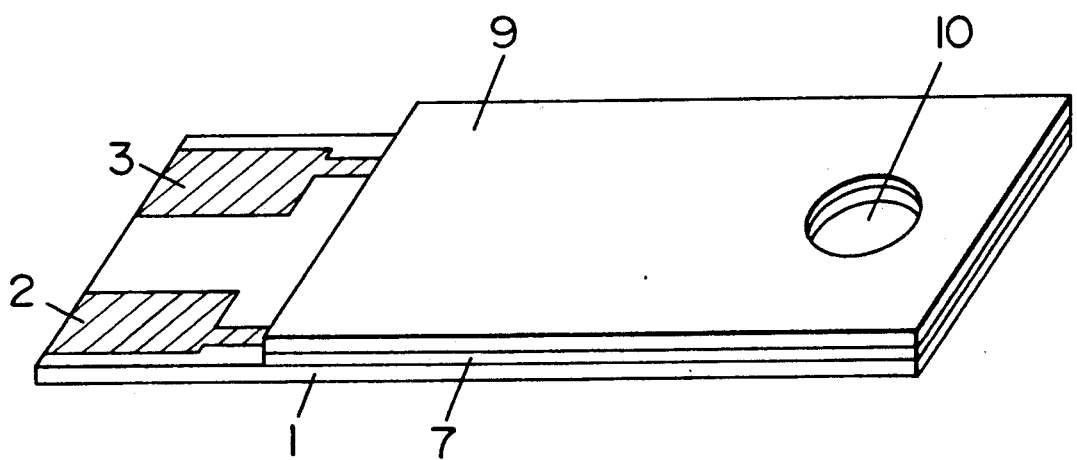
FIG. 9 shows an external view of the biosensor.

In providing the introducing port and the discharge port in the example described above, in addition to the arrangement shown in FIGS. 4 through 6, holes may be provided in the cover 9 and the base plate 1, respectively, and used as the introducing port 10 and the discharge port 11 as shown in the perspective view of the disassembled sensor in FIG. 8 and in the external view in FIG. 9.

Figure 10:
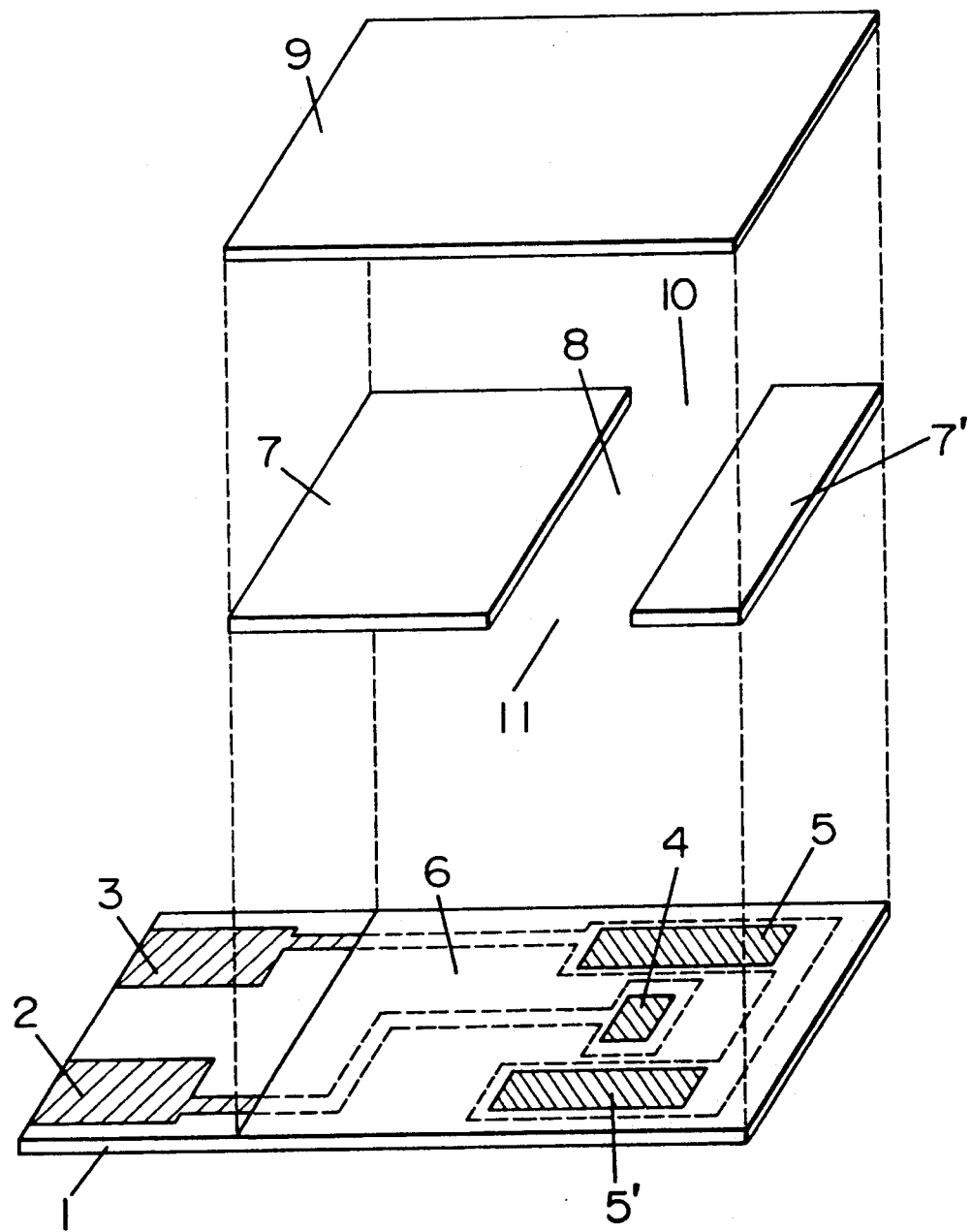
FIGS. 10, 12 and 13 show perspective views of disassembled biosensors which are other embodiments of the present invention.

Furthermore, as shown in the perspective view of the disassembled sensor in FIG. 10, the spacer may be divided into two parts of 7 and 7' and the parts may be used as the spacer 8, and the introducing port 10 and the discharge port 11.

Figure 11:
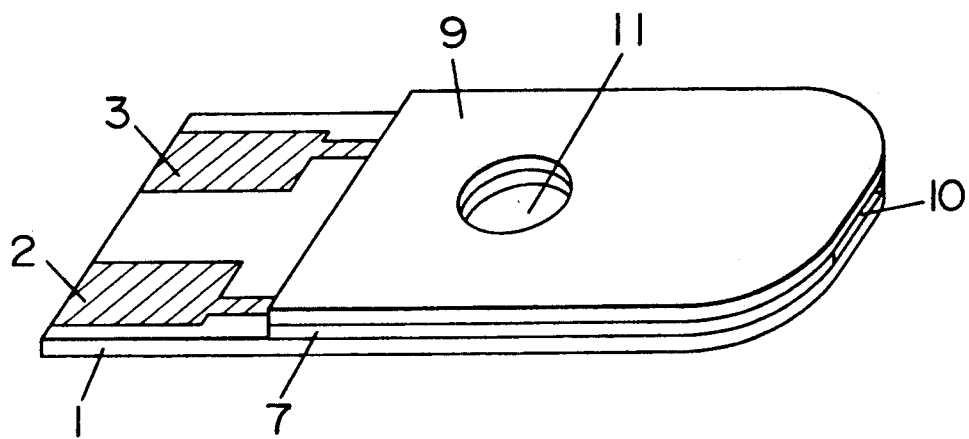
FIG. 11 shows a perspective view of a disassembled biosensor which is another embodiment of the prior art.

Furthermore, the shape of the tip portion of the biosensor having the structure shown in FIG. 5 was rounded as shown in the external view shown in FIG. 11. By doing so, a portion brought into contact with a sample solution was limited almost to the introducing port 10 when the sample solution was introduced. Thus, the sample solution did not go around the periphery of the introducing port but could be smoothly introduced even in a small quantity.

EXAMPLE 3

Figure 12:
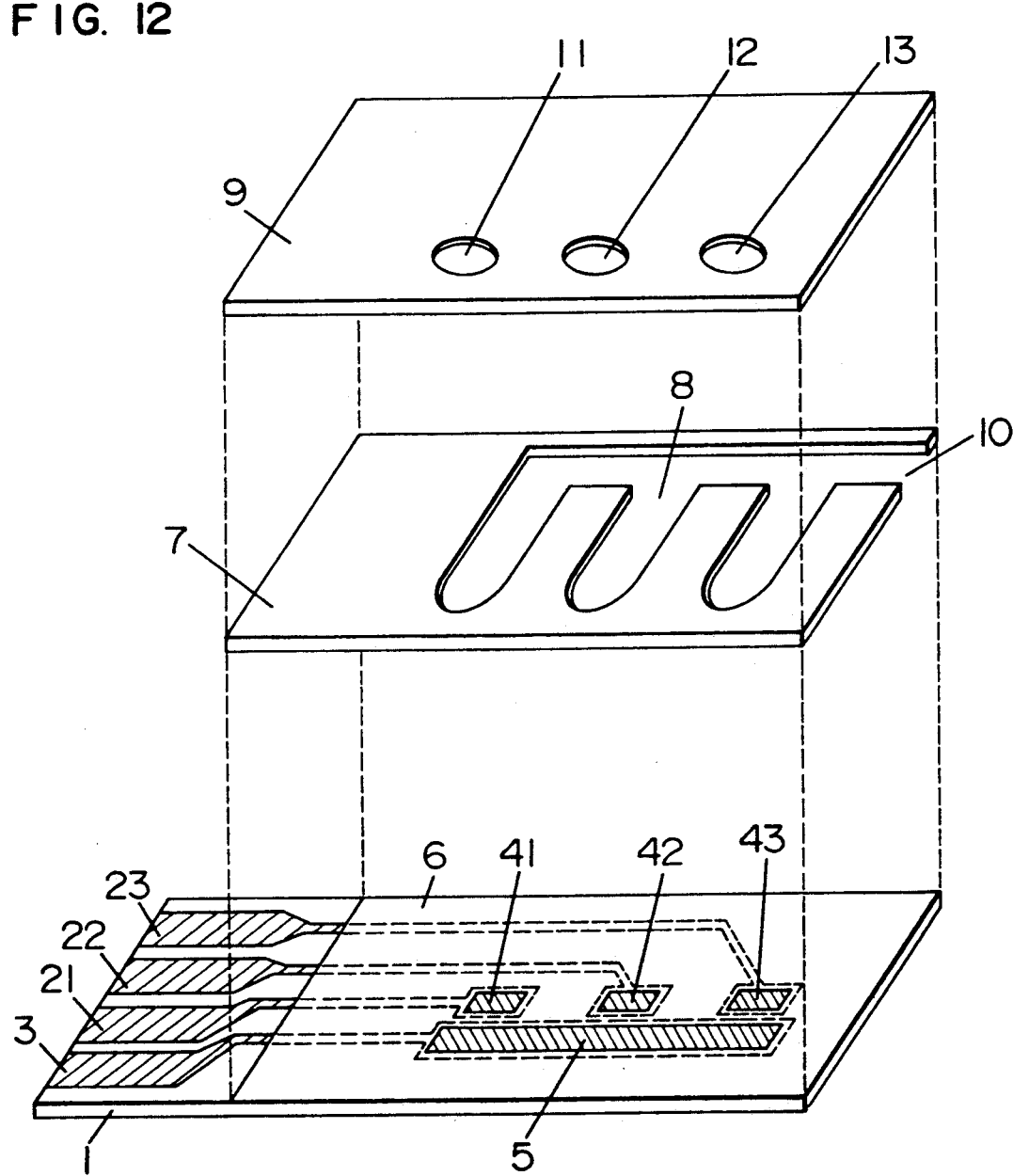

The electrode portion shown in FIG. 12 was constructed in a manner similar to Example 1. That is, silver leads 3, 21, 22 and 23, counter electrode 3 corresponding thereto and three electrodes for measurement 41, 42 and 43 were formed on a base plate to construct three pairs of electrode systems possessing the counter electrode in common. Next, a reaction layer composed of CMC-GOD-electron acceptor layer was formed around each of the electrodes for measurement in a manner similar to Example 2.

Then, a spacer and a cover were adhered to integrate them as in Example 1. Herein, the spacer is partly cut off into a "comb-like" shape and the cut portion forms a space 8. The space is divided into the respective electrode systems but is continuous as a whole to form a common space. Furthermore, the end becomes the introducing port 10.

In response to the space dividedly constructed on these respective electrode systems, three holes are formed in the cover 9 to provide discharge ports 11, 12 and 13. When the introducing port 10 is brought into contact with a sample solution, the sample solution is rapidly introduced into the space, while discharging the air in the space through the three discharge ports.

A response to the glucose standard solution was measured with respect to the three electrode systems in a manner similar to Example 2 and its mean value was determined to make it a response level for one sensor. The test was performed with 30 glucose sensors having the same specification. The coefficient of variation was as good as 2%.

In the disposable type sensor, it is important for improved reliability to minimize factors for error including a difference in electrode area of each sensor. The difference between the sensors forms a cause for causing a difference in error of measurement data on the same sample solution. However, as described above, measurement with higher accuracy can be rapidly achieved by providing a plurality of electrode systems for the same sensor and obtaining a mean value of the response levels.

FIG. 12 shows the embodiment having 3 pairs of electrodes but the present invention is not limited thereto and can further provide a large number of electrode systems. Furthermore, the shape of the space is not limited to those shown in the figures, likewise the shape or arrangement of the electrode systems.

EXAMPLE 4

Figure 13:
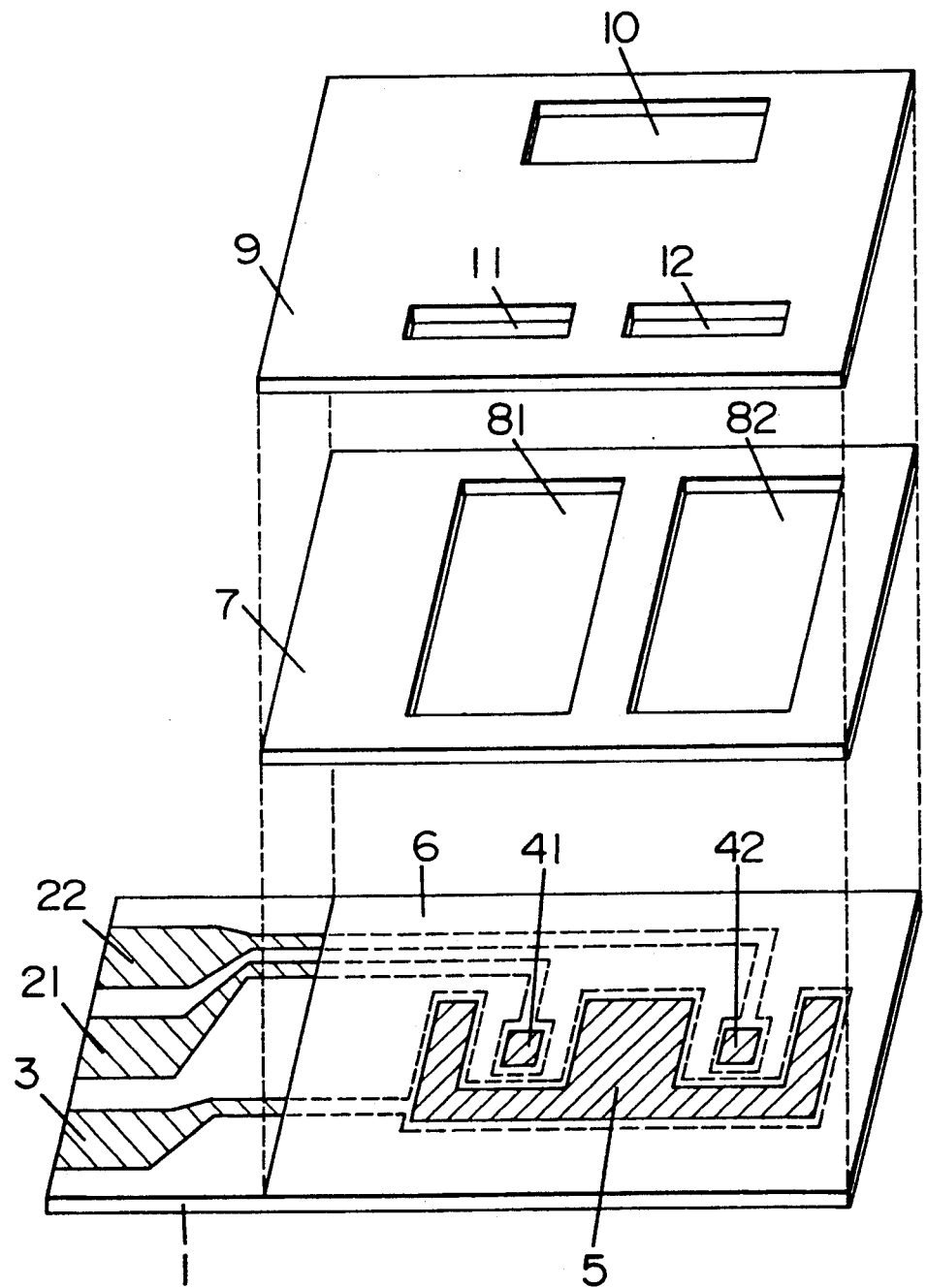

FIG. 13 shows a variation of the construction having a plurality of the electrode systems. In a manner similar to Example 1 already described, silver leads 21, 22 and 3 and two pairs of the electrode systems comprised of electrodes for measurement 41 and 42 corresponding thereto and a counter electrode 5 in common were constructed on the base plate. Next, as in Example 2, after a reaction layer composed of CMC-GOD-potassium ferricyanide layer was formed on each of the electrode systems, a spacer 7 and a cover 9 were adhered thereto. Herein, the spacer has two holes which independently form spaces 81 and 82 and, discharge ports 11 and 12 corresponding to the holes and introducing port 10 used in common are provided in the cover.

With respect to the glucose sensor having the construction described above, as shown in FIG. 3, an average was taken from response values of two pairs of the electrode systems to the glucose standard solution and made a measurement value for one sensor. When 30 sensors having the same specification were tested, the coefficient of variation was as good as 2.2%.

As such, in the sensor shown in FIG. 13, measurement can be made with higher accuracy. In addition, since the sensor possesses the independent spaces, different sample solutions can be measured with one sensor or the sensor can be provided for measurement under different conditions in time, temperature, etc.

In the example described above, one hole was provided in the cover to make it a common introducing port but the present invention is not limited to this embodiment. It is important to construct the measurement system comprising a plural pairs of the electrode systems and a plurality of independent spaces. Therefore, two holes may also be provided and introducing ports to the respective spaces may be constructed.

EXAMPLE 5

Using the electrode part, spacer and cover having constructions shown in FIG. 13, a glucose sensor described below was constructed. Firstly, a reaction layer composed of CMC-GOD was formed on an electrode for measurement 41 in a manner similar to Example 1. On the other hand, CMC layer alone was formed on an electrode for measurement 42.

Figure 14:
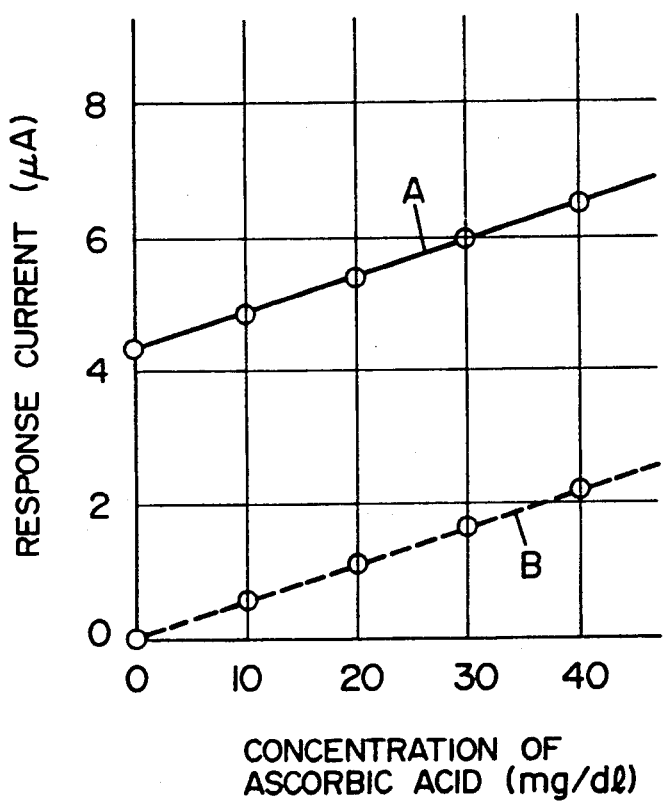
FIG. 14 shows a relationship between ascorbic acid concentration and response characteristic.

With respect to the glucose sensor having two pairs of the electrode systems obtained as described above, a glucose standard solution (200 mg/dl) containing ascorbic acid having various concentrations was dropped onto introducing port 10 and introduced onto each of the electrode systems. Next, as in Example 1, a voltage of 1 V was applied about 1 minute after the dropping and a current level was measured 5 seconds after. The results are shown in FIG. 14. The output of the electrode system of CMC-GOD layer is shown by A and the output (blank output) of the electrode system of CMC layer alone is shown by B. As is evident from the drawing, the output of A increases as the concentration of ascorbic acid increases and on the other hand, a similar increase is noted with the output of B. This indicates that the sensitivities of the respective electrode systems to ascorbic acid are almost equal to each other. When a difference in output between the both electrode systems (A − B) is detected therefrom, a current level based on glucose can be obtained. That is, by using two pairs of the electrode systems, an error due to substances sensitive to electrode can be greatly reduced. Such an effect was also noted with uric acid, etc., in addition to ascorbic acid.

As such, by constructing the sensor by providing two pairs of the electrode systems and forming a hydrophilic high molecular substance-enzyme layer on one electrode system and a hydrophilic high molecular substance layer alone on another electrode system, a substrate concentration in the sample solution containing interferants can be measured with good accuracy.

In the above, after the CMC-GOD layer is formed on both electrode systems, local heating by laser or irradiation with ultraviolet rays, etc. may also be applied only to either electrode system, whereby GOD is inactivated to prepare the electrode system for blank outputting. By doing so, the constructions are identical in the two electrode systems except for enzyme activity so that output currents due to interferants in the two electrode systems can be conformable much better with each other, resulting in an improved accuracy in detection with the sensor.

In the foregoing embodiment, the electrode system wherein the electrode portion comprises two electrodes of the electrode for measurement and the counter electrode has been described. By constructing the electrode system by three electrodes further involving silver/silver chloride, the accuracy can further be improved. One embodiment for constructing the electrode system comprises printing 3 silver leads onto a base plate, then printing a carbon paste only on the tip portions of two leads to coat an insulating layer, treating the surface of the tip portion of the remaining lead in which silver is exposed to form silver chloride into a silver/silver chloride electrode. Thus, the electrode system could be constructed in such a manner.

EXAMPLE 6

In Example 5, a reaction layer composed of CMC-GOD-potassium ferricyanide layer and a layer composed of CMC-potassium ferricyanide were formed on the electrode for measurement 41 and the electrode for measurement 42, respectively, in a manner similar to Example 2. Measurement was performed in a manner similar to Example 5 except that the voltage applied was 0.6 V. Influence of ascorbic acid could be removed as described above.

EXAMPLE 7

In Example 5, a reaction layer composed of CMC-GOD-potassium ferricyanide layer was formed on the electrode for measurement 41 in a manner similar to Example 2. Further on the electrode for measurement 42, the CMC layer was formed and an enzyme layer composed of glucose oxidase, mutarotase and B-glucosidase was then formed thereon and an electron acceptor layer composed of potassium ferricyanide was further formed to make a reaction layer. Measurement was performed by applying a voltage of 0.6 V and using as a sample solution an aqueous solution containing glucose and sucrose. With the electrode for measurement 41, a current in response to glucose concentration was obtained and a current in response to the total concentration of glucose and sucrose was obtained with the electrode for measurement 42. From a difference between these current levels, the sucrose concentration could be determined. As such, two substrate concentrations can be measured.

EXAMPLE 8

After the electrode portion was prepared in a manner similar to Example 1, 0.5 wt % aqueous solution of carboxymethyl cellulose (hereafter simply referred to as CMC) as the hydrophilic high molecular substance was spread onto the electrodes and dried to form a CMC layer. Next, a solution of glucose oxidase in water was spread thereon and dried to form a CMC-GOD layer. In this case, CMC and GOD formed a thin layer having a thickness of several microns in a partly mixed state. Furthermore, 0.5 wt % ethanolic solution of polyvinylpyrrolidone (hereafter simply referred to as PVP) was spread so as to fully cover the first layer composed of this CMC-GOD layer and dried to form a second layer composed of PVP layer. A mixture of microcrystalline potassium ferricyanide as the electron acceptor and 1 wt % solution of a surface active agent, lecithin, in toluene was dropped and spread onto the PVP layer and dried to form a third layer composed of potassium ferricyanide-lecithin layer followed by integrating with a spacer and a cover as in Example 1.

By using toluene in which PVP is sparingly soluble as a solvent in the case of forming the potassium ferricyanide-lecithin layer, it is possible to uniformly spread the potassium ferricyanide-lecithin solution onto the PVP layer. As the result, the uniform potassium ferricyanide-lecithin layer can be obtained.

As such, the use of a solvent in which the hydrophilic high molecular substance constructing the second layer as the solvent for spreading the electron acceptor and the surface active agent could form the extremely uniform electron acceptor layer (third layer).

A glucose standard solution was introduced into the glucose sensor constructed as above through the introducing port. By applying a voltage of +0.6 V to the electrode for measurement in the anode direction one minute after, a response current was measured 5 seconds. A good linear relationship was obtained up to the concentration as high as more than 900 mg/dl. Onto the glucose sensor described above, 5 µl of blood sample was dropped and a response current was measured one minute after. A response with very good reproducibility was obtained.

With respect to two sensors, i.e., the glucose sensor prepared by the process described above and the same glucose sensor except that the second layer composed of hydrophilic high molecular substance was not provided, preservation test was performed at 35° C. for 30 days in a dried state. Using a glucose standard solution (90 mg/dl) as a sample solution, sensor response was compared 30 days after. The sensor in which the second layer composed of the hydrophilic high molecular substance was not formed showed the coefficient of variation of 5.3% but the sensor in which the second layer composed of PVP showed the coefficient of variation as extremely good as 2.5%.

EXAMPLE 9

The CMC-GOD layer and the PVP layer were prepared in a manner similar to Example 8. A mixture of microcrystalline potassium ferricyanide as the electron acceptor and 0.5 wt % solution of a surface active agent, lecithin, in ethanol was dropped and spread onto the PVP layer and dried to form a potassium ferricyanide-lecithin layer. By using ethanol in which PVP is readily soluble as a solvent in the case of forming the potassium ferricyanide-lecithin layer, it is possible to concentratively develop at one point on the PVP layer. That is, it was possible to concentrate on the electrode for measurement of the sensor to construct the uniform potassium ferricyanide-lecithin layer so that the sensor in which a stable response was obtained merely by spreading the minimum quantity required could be prepared.

Response characteristics to the glucose standard solution of the glucose sensor constructed as above were determined in a manner similar to Example 8. A good linear relationship was obtained up to the concentration as high as more than 900 mg/dl. In addition, a response with very good reproducibility was obtained also in the case of using blood as a sample solution. Furthermore, with respect to the glucose sensor in which the second layer composed of hydrophilic high molecular substance was provided and the same glucose sensor except that the second layer composed of hydrophilic high molecular substance was not provided, preservation test was performed at 35° C. for 30 days in a dried state in a manner similar to Example 8. The sensor in which the second layer composed of PVP showed extremely good coefficient of variation, in the response measured 30 days after.

In the prior art construction, the GOD-CMC layer was already in contact with the potassium ferricyanide-lecithin layer at the time when the sensor was prepared so that it was difficult to improve preservation efficiency. The hydrophilic high molecular substance layer composed of PVP which was used in Example 8 described above and present Example 9 takes a role to completely separate the GOD-CMC layer from the potassium ferricyanide-lecithin layer in a dried state.

In addition, the hydrophilic high molecular substance layer is extremely effective to ensure a stable sensor response, also in the case that substances readily adsorbed to the electrode or electrode-active substances are present in a sample solution. Even in the case that a glucose concentration was determined by the glucose sensor described above using blood as a sample solution, a stable sensor response was obtained irrespective of viscosity or the like of the sample solution.

In Examples 1 through 9 described above, one embodiment of preferred positional relationship between the introducing port and the discharge port connected the space is illustratively shown in the drawings. The discharge port may also be used as the introducing port and the introducing port may be used as the discharge port. Furthermore, the spacers and the covers shown in the respective drawings are composed of independent materials but are not limited thereto. It is advantageous in mass production to form an integrated cover member with a shape of cover by means of molding or the like.

Further by rendering the surface of materials constructing the space hydrophilic, a sample solution was introduced more smoothly through the introducing port. The effect was obtained either by using hydrophilic materials or by previously treating the surface materials constructing the space with a surface active agent to render them hydrophilic.

On the other hand, an interval between the base plate and the cover can be controlled by varying the thickness of spacer or the size of a portion corresponding thereto. However, when the interval is too large, a quantity of sample solution required for filling up the space becomes large and it is also disadvantageous to introduce the sample solution by capillary phenomenon. When the interval is too small, a resistance between the electrodes increases or a current distribution is distorted. From the foregoing, the interval is preferably in a range of 0.05 to 1.0 mm, more preferably 0.1 to 0.5 mm.

In the examples, CMC was used as the hydrophilic high molecular substance. As has already been stated, its role is to prevent influence of adsorbable substances contained in a sample solution adsorbed to the electrode on response, in addition to the smooth introduction of the sample solution. Furthermore, its role also lies in separating the enzyme layer from the electron acceptor layer by the hydrophilic high molecular substance layer thereby to further improve preservation property. As the hydrophilic high molecular substance, gelatin, methyl cellulose and the like can be used, in addition to CMC, and hydrophilic high molecular substances of starch, carboxymethyl cellulose, gelatin, acrylate, vinyl alcohol, vinylpyrrolidone and maleic anhydride are preferred. These water-absorbing or water-soluble hydrophilic high molecular substances are dissolved in a suitable concentration and the resulting solution is coated and dried to form a hydrophilic high molecular substance layer having a necessary layer thickness.

In the foregoing examples, the electrode system in which the electrode portion is comprised of two electrodes of an electrode for measurement and a counter electrode has been stated. However, by constructing the electrode system with three electrodes further including a reference electrode, the accuracy can be further improved. As materials for the electrode, carbon illustrated in the examples is suitable as a stable and inexpensive material but the materials are not limited thereto. Other noble metal materials and oxidized materials may also be used.

Further as the electron acceptor, though potassium ferricyanide used in the examples is excellent in stability and reaction rate, redox compounds such as quinone compounds or ferrocene compounds, etc. can also be used, in addition to potassium ferricyanide.

Furthermore, the oxidoreductase is not limited to glucose oxidase shown in the foregoing examples but various enzymes such as alcohol oxidase, cholesterol oxidase, etc. can be used.

INDUSTRIAL APPLICABILITY

The biosensor of the present invention can rapidly determine a specific component in various sample solutions in an accurate and simple way. Therefore, its utilization value is extremely high in clinical inspection.

We claim:

1. A biosensor for determining a substrate concentration in a sample solution comprising a base plate having an electrode system and a reaction layer having formed thereon a space including said reaction layer, said space being provided with an introducing port for introducing said sample solution into said space and a discharge port for discharging the gas in said space by inflow of said sample solution, said electrode system being equipped with at least an electrode for measurement and a counter electrode, at least an enzyme being carried on said reaction layer, a change in concentration of a substance in the reaction between said enzyme and said sample solution being detected with said electrode system to determine a substrate concentration in said sample solution.

2. A biosensor as claimed in claim 1, wherein said electrode system comprises a plural set of electrode systems and reaction layers corresponding to said plural set of electrode systems and a common space are provided.

3. A biosensor as claimed in claim 1, wherein said electrode system comprises a plural set of electrode systems and, reaction layers and spaces corresponding to said plural set of electrode systems are provided.

4. A biosensor as claimed in claim 1, wherein an electrode system comprising at least an electrode for measurement and a counter electrode is formed on an insulating base plate, a reaction layer is formed on the surface of said electrode system and said reaction layer comprises an enzyme layer composed of an oxidoreductase and a hydrophilic high molecular substance having formed thereon an electron acceptor layer.

5. A biosensor as claimed in claim 1, wherein an electrode system comprising at least an electrode for measurement and a counter electrode is formed on an insulating base plate, a reaction layer is formed on the surface of said electrode system and said reaction layer comprises an enzyme layer composed of an oxidoreductase and a hydrophilic high molecular substance having formed thereon an electron acceptor layer containing a surface active agent.

6. A biosensor as claimed in claim 4 or 5, wherein said electron acceptor layer comprises fine particles of an electron acceptor having a particle size of not greater than 100 $\mu$m.

7. A biosensor as claimed in claim 4 or 5, wherein said hydrophilic high molecular substance is any member selected from hydrophilic high molecular substances of starch, carboxymethyl cellulose, gelatin, acrylate, vinyl alcohol, vinylpyrrolidone and maleic anhydride or a mixture thereof.

8. A biosensor as claimed in claim 1, wherein the surface of a material constructing said space is hydrophilic.

9. A biosensor as claimed in claim 2 or 3, wherein said electrode system comprises two sets of electrode systems comprising at least an electrode for measurement and a counter electrode mainly composed of carbon, a reaction layer composed of a hydrophilic high molecular substance and an oxidoreductase being provided on one electrode system and a hydrophilic high molecular substance layer or a layer composed of a hydrophilic high molecular substance and an inactivated oxidoreductase being provided on another electrode system.

10. A biosensor as claimed in claim 2 or 3, wherein said electrode system comprises two sets of electrode systems comprising at least an electrode for measurement and a counter electrode mainly composed of carbon, a reaction layer composed of a hydrophilic high molecular substance and an oxidoreductase being provided on one electrode system and a hydrophilic high molecular substance layer or a layer composed of a hydrophilic high molecular substance and a deactivated oxido-reductase being provided on another electrode system.

11. A biosensor as claimed in claim 9 or 10, wherein said electrode system comprises an electrode for measurement and a counter electrode mainly composed of carbon and a reference electrode comprising a silver/silver chloride.

12. A biosensor as claimed in claim 1, wherein said electrode system is prepared from a material mainly composed of carbon formed on an insulating base plate by means of screen printing.

13. A biosensor as claimed in claim 1, wherein an electrode system comprising at least an electrode for measurement and a counter electrode is formed on an insulating base plate, a reaction layer is formed on said electrode system and said reaction layer comprises a first layer composed of a hydrophilic high molecular substance and an oxidoreductase, a second layer composed of a hydrophilic high molecular substance and a third layer containing an electron acceptor.

14. A biosensor as claimed in claim 13, wherein said hydrophilic high molecular substance in the first layer and the second layer is selected from hydrophilic high molecular substances of starch, carboxymethyl cellulose, gelatin, acrylate, vinyl alcohol, vinylpyrrolidone and maleic anhydride or a mixture thereof.

15. A process for preparing a biosensor which comprises forming an electrode system comprising at least an electrode for measurement and a counter electrode on an insulating base plate, coating a hydrophilic high molecular substance aqueous solution and an oxidoreductase aqueous solution on said electrode system and then drying to form an enzyme layer, spreading a mixture of an electron acceptor and an organic solvent onto said enzyme layer, removing said organic solvent to form an electron acceptor layer and then integrating together with a cover.

16. A process for preparing a biosensor which comprises forming an electrode system comprising at least an electrode for measurement and a counter electrode on an insulating base plate, coating a hydrophilic high molecular substance aqueous solution and an oxidoreductase aqueous solution on said electrode system and then drying to form an enzyme layer, next spreading a solution of a hydrophilic high molecular substance in an organic solvent onto said enzyme layer to form a hydrophilic high molecular substance layer, further spreading a dispersion of an electron acceptor in an organic solvent onto said hydrophilic high molecular substance layer to form an electron acceptor layer, and then integrating together with a cover.

17. A process for preparing a biosensor as claimed in claim 15 or 16, wherein a mixture of said electron acceptor, said surface active agent and said organic solvent is spread on said enzyme layer and said organic solvent is removed to form an electron acceptor layer.

18. A process for preparing a biosensor as claimed in claim 17, wherein said electron acceptor layer comprises fine particles of an electron acceptor having a particle size of not greater than 100 $\mu$m.

* * * * *

UNITED STATES PATENT AND TRADEMARK OFFICE
CERTIFICATE OF CORRECTION

PATENT NO. : 5,120,420

DATED : June 9, 1992

INVENTOR(S) : Shiro NANKAI et al

It is certified that error appears in the above-identified patent and that said Letters Patent is hereby corrected as shown below:

Title Page, after "[22] PCT Filed:" the date should be

--Mar. 30, 1989--.

Signed and Sealed this

Ninth Day of November, 1993

Attest:

BRUCE LEHMAN

*Attesting Officer*     *Commissioner of Patents and Trademarks*

REEXAMINATION CERTIFICATE (3924th)

United States Patent [19]
Nankai et al.

[11] B1 5,120,420
[45] Certificate Issued Nov. 9, 1999

[54] BIOSENSOR AND A PROCESS FOR PREPARATION THEREOF

[75] Inventors: Shiro Nankai, Hirakata; Mariko Kawaguri; Mayumi Obtani, both of Moriguchi; Takashi Iijima, Hirakata, all of Japan

[73] Assignee: Matsushita Electric Industrial Co., Ltd., Kadoma, Japan

Reexamination Request:
No. 90/005,085, Aug. 26, 1998

Reexamination Certificate for:
Patent No.: 5,120,420
Issued: Jun. 9, 1992
Appl. No.: 07/445,632
Filed: Nov. 27, 1989

Certificate of Correction issued Nov. 9, 1993.

[22] PCT Filed: Mar. 30, 1989
[86] PCT No.: PCT/JP89/00337
§ 371 Date: Jan. 31, 1990
§ 102(e) Date: Jan. 31, 1990
[87] PCT Pub. No.: WO89/09397
PCT Pub. Date: Oct. 5, 1989

[30] Foreign Application Priority Data

Mar. 31, 1988 [JP] Japan .................................. 63-080829
Mar. 31, 1988 [JP] Japan .................................. 63-080842
May 18, 1988 [JP] Japan .................................. 63-121002

[51] Int. Cl.$^6$ .................................................. G01N 27/26
[52] U.S. Cl. .......................... 204/403; 204/415; 205/778; 205/782.5; 435/817; 435/180; 436/531; 436/806
[58] Field of Search .................................. 204/403, 415; 205/778, 782.5; 435/817, 180; 436/531, 806

[56] References Cited

U.S. PATENT DOCUMENTS

| | | | |
|---|---|---|---|
| 3,838,033 | 9/1974 | Mindt et al. | 204/195 |
| 3,979,274 | 9/1976 | Newman | 204/195 B |
| 3,993,451 | 11/1976 | Verbeck | 23/253 TP |
| 4,053,381 | 10/1977 | Hamblen et al. | 204/195 M |
| 4,137,495 | 1/1979 | Brown | 324/30 B |

(List continued on next page.)

FOREIGN PATENT DOCUMENTS

| | | |
|---|---|---|
| 016387 | 10/1980 | European Pat. Off. . |
| 078636 | 5/1983 | European Pat. Off. . |
| 115873 | 8/1984 | European Pat. Off. . |
| 121385 | 10/1984 | European Pat. Off. . |
| 127958 | 12/1984 | European Pat. Off. . |

(List continued on next page.)

OTHER PUBLICATIONS

Karl Schugerl et al.; *Online–Prozessanalyse in Bioreatoren;* Chem.–Ing.–Tech.; 59 (1987) Nr. 9, S. 701–714 Translation attached. *No month available.

*Primary Examiner*—Bruce F. Bell

[57] ABSTRACT

A biosensor of the invention comprises an insulating base board (1) having formed thereon, in sequence, leads (2, 3, 3'), an electrode system mainly made of carbon (4, 5, 5'), an insulating layer (6) and a reaction layer (14) composed of an enzyme and an electron acceptor, and being provided thereon with a space (8) defined by a spacer (7) and a cover 9). When a biological sample solution is brought into contact with the inlet (10) of the biosensor having the above-described structure, the sample solution is introduced into its inside, while the air within the space (8) is rapidly discharged through the outlet (11) and, at the same time, the space (8) is filled with the sample solution up to the neighborhood of the outlet. Thus, measurement can be conducted inexpensively at a high speed with a high accuracy through simple procedures without residual bubbles.

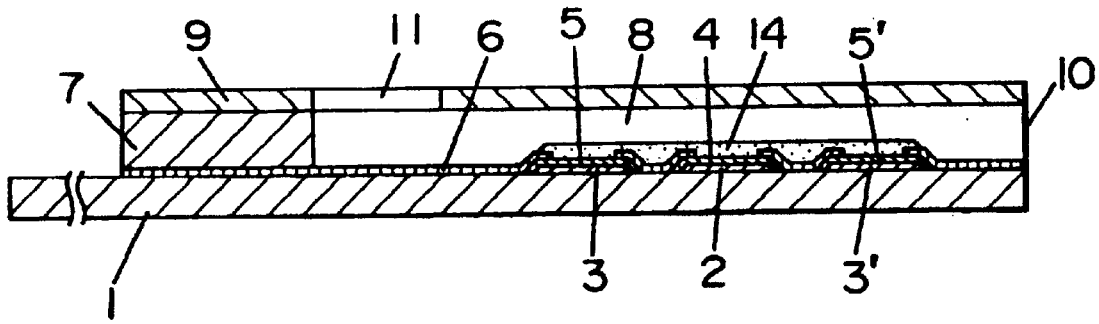

U.S. PATENT DOCUMENTS

| Number | Date | Inventor | Class |
|---|---|---|---|
| 4,216,245 | 8/1980 | Johnson | 427/2 |
| 4,225,410 | 9/1980 | Pace | 204/195 R |
| 4,233,029 | 11/1980 | Columbus | 23/230 R |
| 4,273,639 | 6/1981 | Gottermeir | 204/195 R |
| 4,301,412 | 11/1981 | Hill et al. | 324/442 |
| 4,301,414 | 11/1981 | Hill et al. | 324/446 |
| 4,303,887 | 12/1981 | Hill et al. | 324/441 |
| 4,312,834 | 1/1982 | Vogel et al. | 422/56 |
| 4,413,407 | 11/1983 | Columbus | 29/825 |
| 4,418,148 | 11/1983 | Oberhardt | 435/179 |
| 4,473,457 | 9/1984 | Columbus | 204/416 |
| 4,490,216 | 12/1984 | McConnell | 204/1 T |
| 4,502,938 | 3/1985 | Covington et al. | 204/412 |
| 4,545,382 | 10/1985 | Higgins et al. | 128/635 |
| 4,591,550 | 5/1986 | Hafeman et al. | 435/4 |
| 4,654,127 | 3/1987 | Baker et al. | 204/195 B |
| 4,654,197 | 3/1987 | Lilja et al. | 422/56 |
| 4,897,173 | 1/1990 | Nankai et al. | 204/403 |
| 4,900,405 | 2/1990 | Otagawa et al. | 204/1 T |
| 5,108,564 | 4/1992 | Szuminsky et al. | 204/153.12 |
| 5,128,015 | 7/1992 | Szuminsky et al. | 204/403 |
| 5,185,256 | 2/1993 | Nankai et al. | 435/174 |
| 5,509,410 | 4/1996 | Hill et al. | 128/637 |
| 5,682,884 | 11/1997 | Hill et al. | 128/637 |
| 5,727,548 | 3/1998 | Hill et al. | 128/637 |
| 5,820,551 | 10/1998 | Hill et al. | 600/347 |

FOREIGN PATENT DOCUMENTS

| Number | Date | Country |
|---|---|---|
| 136362 | 4/1985 | European Pat. Off. . |
| 096095 | 11/1985 | European Pat. Off. . |
| 170375 | 2/1986 | European Pat. Off. . |
| 171148 | 2/1986 | European Pat. Off. . |
| 186286 | 7/1986 | European Pat. Off. . |
| 200539 | 11/1986 | European Pat. Off. . |
| 230472 | 8/1987 | European Pat. Off. . |
| 255291 | 2/1988 | European Pat. Off. . |
| 267724 | 5/1988 | European Pat. Off. . |
| 59-040145 | 3/1984 | Japan . |
| 62-137559 | 6/1987 | Japan . |
| 62-237348 | 10/1987 | Japan . |
| 63-003248 | 1/1988 | Japan . |
| 63-058149 | 3/1988 | Japan . |
| 63-144245 | 6/1988 | Japan . |
| 63-144246 | 6/1988 | Japan . |
| 63-144247 | 6/1988 | Japan . |
| 01023152 | 1/1989 | Japan . |
| 01023153 | 1/1989 | Japan . |
| 01023154 | 1/1989 | Japan . |
| 01114746 | 5/1989 | Japan . |
| 01114747 | 5/1989 | Japan . |
| 01134242 | 5/1989 | Japan . |
| 01134243 | 5/1989 | Japan . |
| 01134244 | 5/1989 | Japan . |
| 01212345 | 8/1989 | Japan . |
| 1318815 | 5/1973 | United Kingdom . |
| 2090659 | 6/1982 | United Kingdom . |
| 88/03270 | 5/1988 | WIPO . |
| 8908713 | 9/1989 | WIPO . |

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 15–18 is confirmed.

Claim 1 is determined to be patentable as amended.

Claims 2–14, dependent on an amended claim, are determined to be patentable.

New claims 19–26 are added and determined to be patentable.

1. A biosensor for determining a substrate concentration in a sample solution comprising a base plate having an electrode system and a reaction layer, having formed thereon a space including said reaction layer, said space being provided with an introducing port for introducing said sample solution into said space and a discharge port for discharging the gas in said space by inflow of said sample solution, said electrode system being equipped with at least an electrode for measurement and a counter electrode, at least an enzyme being carried on said reaction layer, a change in concentration of a substance in the reaction between said enzyme and said sample solution being detected with said electrode system to determine a substrate concentration in said sample solution, *wherein said reaction layer is positioned over both said electrode for measurement and said counter electrode.*

19. *A biosensor for determining a substrate concentration in a sample solution comprising a base plate having an electrode system and a reaction layer, having formed thereon a space including said reaction layer, said space being provided with an introducing port for introducing said sample solution into said space and a discharge port for dicharging the gas in said space by inflow of said sample solution, said electrode system being equipped with at least an electrode for measurement and a counter electrode, at least an enzyme being carried on said reaction layer, a change in concentration of a substance in the reaction between said enzyme and said sample solution being detected with said electrode system to determine a substrate concentration in said sample solution, wherein at least a portion of the surface of said space is hydrophilic.*

20. *A biosensor as claimed in claim 19, wherein at least a portion of said space is coated with a component to render said portion of said space hydrophilic.*

21. *A biosensor as claimed in claim 20, wherein said component is selected from the group consisting of starch, carboxymethyl cellulose, gelatin, acrylate, vinyl alcohol, vinylpyrrolidone and maleic anhydride or a mixture thereof.*

22. *A biosensor as claimed in claim 20, wherein said component comprises a surface active agent.*

23. *A biosensor for determining a substrate concentration in a sample solution comprising a base plate having an electrode system and a reaction layer, having formed thereon a space including said reaction layer, said space being provided with an introducing port for introducing said sample solution into said space and a discharge port for dicharging the gas in said space by inflow of said sample solution, said electrode system being equipped with at least an electrode for measurement and a counter electrode, at least an enzyme being carried on said reaction layer, a change in concentration of a substance in the reaction between said enzyme and said sample solution being detected with said electrode system to determine a substrate concentration in said sample solution, wherein the reaction layer further comprises a component to reduce influence of an unwanted constituent to at least one electrode, wherein the unwanted constituent is selected from the group consisting of adsorbable substances and solid components.*

24. *A biosensor as claimed in claim 23, wherein said solid components comprise red blood cells.*

25. *A biosensor for determining a substrate concentration in a sample solution comprising a base plate having an electrode system and a reaction layer, having formed thereon a space including said reaction layer, said space being provided with an introducing port for introducing said sample solution into said space and a discharge port for discharging the gas in said space by inflow of said sample solution, said electrode system being equipped with at least an electrode for measurement and a counter electrode, at least an enzyme being carried on said reaction layer, a change in concentration of a substance in the reaction between said enzyme and said sample solution being detected with said electrode system to determine a substrate concentration in said sample solution, wherein said reaction layer further comprises a hydrophilic high molecular substance and said reaction layer is formed directly covering at least one electrode.*

26. *A biosensor as claimed in claim 25, wherein said hydrophilic high molecular substance is selected from the group consisting of starch, carboxymethyl cellulose, gelatin, acrylate, vinyl alcohol, vinylpyrrolidone and maleic anhydride or a mixture thereof.*

\* \* \* \* \*